US006805121B1

(12) United States Patent
Flood et al.

(10) Patent No.: US 6,805,121 B1
(45) Date of Patent: Oct. 19, 2004

(54) ANTI-G PRESSURE REGULATOR FOR SUPPLYING BREATHABLE GAS TO A PILOT'S FACE MASK AND METHOD

(75) Inventors: Michael G. Flood, 4525 Bohemia Pl., Pensacola, FL (US) 32504; Robert M. Hamilton, Brea, CA (US)

(73) Assignee: Michael G. Flood

( * ) Notice: Subject to any disclaimer, the term of this patent is extended or adjusted under 35 U.S.C. 154(b) by 148 days.

(21) Appl. No.: 10/091,926

(22) Filed: Mar. 5, 2002

Related U.S. Application Data

(60) Provisional application No. 60/274,332, filed on Mar. 8, 2001.

(51) Int. Cl.$^7$ .............................................. A61M 16/00

(52) U.S. Cl. ............................ 128/204.26; 128/202.11; 128/202.12; 128/204.18; 128/204.23; 128/205.24

(58) Field of Search ...................... 128/202.11, 201.24, 128/205.26, 204.23, 204.26, 204.18, 205.24, 205.25; 600/19, 12, 20

(56) References Cited

U.S. PATENT DOCUMENTS 4,219,039 A * 8/1980 Jaggars ........................ 137/38
4,336,590 A * 6/1982 Jacq et al. ............. 128/204.21
4,638,791 A * 1/1987 Krogh et al. ................. 600/19
5,170,814 A * 12/1992 Crome ........................ 137/39
5,199,426 A * 4/1993 Aldworth et al. ...... 128/205.24
5,269,295 A * 12/1993 Foote et al. ........... 128/204.18
5,314,402 A * 5/1994 Foote et al. .................. 600/20
5,477,850 A * 12/1995 Zegler et al. .......... 128/202.11
5,701,889 A * 12/1997 Danon ................... 128/204.29

OTHER PUBLICATIONS

Excerpt from an article entitled Combined Advanced Technology Enhanced Design G–ensemble—Advanced. Technology Anti G–Suit—Combat Edge Aircrew Positive Pressure Breathing System published by Brooks Scientific and Research Center of Space Medicine in San Antonio, TX.

* cited by examiner

*Primary Examiner*—Glenn K. Dawson
*Assistant Examiner*—Darwin P Erezo
(74) *Attorney, Agent, or Firm*—Harold L. Jackson

(57) ABSTRACT

An anti-g pressure regulator functions, in conjunction with a pressurized anti-g suit during high g loads, to supply $O_2$ to a pilot's face mask during the inhalation phase with the $O_2$ pressure rising from a predetermined minimum to a predetermined maximum as determined by the g load to increase the volume of $O_2$ supplied to the pilot's lungs. During the exhalation phase the pressure is allowed to fall from the maximum to the minimum to reduce the stress experienced by the pilot during exhalation thereby enabling the pilot to tolerate high g loads. Optionally, the pressure of gas supplied to the anti-g suit may be controlled in a nonlinear manner with respect to the anticipated range of g-loads to improve the pilot's performance during exposure to intermediate g-loads.

23 Claims, 12 Drawing Sheets

PRIOR ART

BREATHING

ANTI-G PRESSURE REGULATOR FOR SUPPLYING BREATHABLE GAS TO A PILOT'S FACE MASK AND METHOD

RELATED APPLICATION

This application claims the benefit of the filing date of provisional application No. 60/274,332, filed Mar. 8, 2001, entitled ANTI-G PRESSURE REGULATOR FOR SUPPLYING BREATHABLE GAS TO A PILOT'S FACE MASK AND METHOD as to all common subject matter.

FIELD OF THE INVENTION

The present invention relates to life support equipment and methods for providing physiological protection to pilots and astronauts when subjected to high g-force maneuvers.

BACKGROUND OF THE INVENTION

Modem aircraft are capable of maneuvers which can impose multiple gravity ("g") forces which exceed the physiological protection provided by state of the art life support equipment. Such equipment includes an anti-g suit with pneumatic bladders surrounding a major portion of a pilot's legs, thighs and abdomen, which when inflated impede the flow of blood to the lower extremities and abdomen. In addition, a chest bladder is often used to restrain excess chest expansion during the inhalation of oxygen (or oxygen enriched air) at elevated pressures. A mask, fitted over the pilot's nose and mouth, receives oxygen or a mixture of oxygen and air under a pressure proportional to the g-force loading to which the pilot is subjected.

A typical anti-g equipment arrangement for use by combat and test pilots is illustrated in FIG. 1 in which a source 11 of a suitable gas, such as air under a suitable pressure from an aircraft's compressor is connected to a pressure regulator 12. A source 10 of oxygen or oxygen enriched air (hereinafter collectively referred to as $O_2$) under a suitable high pressure, e.g., 1.5 to 10.0 atmospheres or about 22 to 150 psi, is connected to separate pressure regulator 12. The regulator 12 supplies the air, via line 16, to a conventional anti-g suit 18 which fits over the legs and lower abdomen of the pilot. The anti-g suit includes a series of inflatable bladders 18*a*. The regulator 14 supplies $O_2$ to a chest bladder 20 and a face mask 22 via line 24.

Conventional g-force sensors (not shown) control the regulators 12 and 14 so that the output pressures thereof are a function of the g-forces to which the pilot is being subjected. FIG. 2 illustrates, via curve 24, the typical pressure in millimeters, of Hg (ordinate) applied to the anti-g suit as a function of the g-force (abscissa). As is illustrated, the pressure curve 24 is essentially linear with changes in the g-force loading from about 1 g to about 10 g's.

FIG. 3 illustrates, via curve 26, the typical pressure in inches of water (ordinate) applied to the chest bladder and the inlet to the mask as a function of the g-force loading. From about 4 g's to 10 g's the curve is essentially linear.

The mask 22 is provided with a conventional inhalation and exhalation valves (not shown). The exhalation valve remains closed until the pressure of the gas to be exhaled exceeds the positive pressure being supplied by the regulator 14. The pilot must therefore exert sufficient pressure on his or her lungs during the exhalation phase to overcome the positive supply pressure. The maximum exhalation pressure may exceed the supply pressure by 5 to 6 inches of $H_2O$ during a normal breathing cycle. A typical pilot's inhalation and exhalation phases, using the conventional anti-g equipment, is illustrated in FIG. 4 where the line 28 represents one value of positive supply pressure (as measured along the ordinate) and the curve 30 represents the pressure in the mask during the pilot's inhalation ($t_0$–$t_1$) and exhalation ($t_1$–$t_2$) phases. As is noted by the curve 30 the pressure in the mask follows a sinusoidal type curve during the breathing cycle. The extent of the fluctuations in mask pressure from the supply pressure depend on the gas capacity of the system and on the resistance of the mask regulator system. Such a state of the art system is discussed in several articles entitled *Combined Advanced Technology Enhanced Design G-ensemble; Advanced Technology Anti G-Suit; and Combat Edge Aircrew Positive Pressure Breathing System* published by the Brooks Scientific and Research Center of Space Medicine in San Antonio, Tex. and posted on its website at http://www.brooks.af.mil/HSW/products/edge.html.

At high g-forces, e.g., above 3–4 g's, the state of the art anti-g equipment provides a constant positive pressure in the mask and vest. Such a pressure mode places little stress on a pilot's system during inhalation. However, the positive pressure in the lungs and internal chest pressure causes the diaphragm to lower. In order to raise the diaphragm and help the breathing muscles to perform an exhalation and subsequent inhalation exercise it is necessary for the pilot to strain and release the abdominal muscles periodically. This is especially difficult at very high g-forces. With abdominal muscles in a strained condition and an impaired or non-functioning diaphragm, the breathing muscles cannot provide normal breathing. The exhalation and inhalation phases become shorter, i.e., the breathing rate and lung ventilation increase. The velocity of air flow through the exhalation valve increases during the shortened inhalation phase resulting in a higher resistance to exhalation which may reach 9–10 mm of mercury column. The increased stress not only causes the pilot to feel fatigue, but degrades his or her performance. At the same time blood slowly moves down from the brain as his or her higher heart rate indicates.

State of the art anti-g systems typically provide satisfactory physiological protection during force loads up to 8–9 g's for only 30 to 40 seconds.

As a result, such conventional anti-g equipment will not accommodate the full performance capabilities of modem fighter aircraft. Thus, due to the limited time of high g tolerance, the pilot must restrict the aircraft's performance to levels below its rated capabilities or run the risk of suffering sever fatigue at best or losing control of the aircraft at worst. In addition, the constant positive exhalation pressure at high g loads severely limits or precludes two-way radio communication with the attendant disadvantages thereof during maneuvering. Also pilots experience extreme discomfort when breathing at high g loads with the result that their physical condition may be impaired for some time after the cessation of a high g maneuver.

A pilot's breathing rate is typically drastically increased by the higher exhalation resistance (FIG. 4), e.g., 40–50+ liters/min at 7–9 g force loads versus about 20 liters/min at no g load. Very often pilots complain of feeling severe pain in their hand joints due to the lack of compensating pressure. Immediately after long term exposure to high g forces, pilots have pointed out that their breathing does not return to normal for some time and that several days of rest may and often are required for rehabilitation after an intensive workout during flight. The long term effects on a pilot's health resulting from the wear and tear on the organisms, e.g., those involved in the breathing and cardiovascular systems which results from regular g force overloads over an extended period have not been determined.

There is an urgent need to provide combat and test pilots with greater physiological protection from the effects of high g maneuvers.

SUMMARY OF THE INVENTION

In accordance with the present invention a pilot is equipped with an anti-g suit which is inflated from a pressurized gas, e.g., air, in accordance with the g forces being experienced by the pilot in a conventional manner.

A method and apparatus of overcoming the shortcomings of conventional anti-g equipment for providing physiological protection for pilots when subjected to high g-forces includes the use of an inhalation valve connected between a pressurized source of $O_2$, an inlet/outlet port of the pilot's face mask and a chest bladder.

An exhalation valve is connected between the inlet/outlet port and a low pressure region such as the aircraft cabin interior. The inhalation and exhalation valves are opened and closed, respectively, during the inhalation phase of the pilot's spontaneous breathing cycle while the pressure of the $O_2$ supplied to the inlet/outlet port is controlled so that the pressure rises from a predetermined minimum to a predetermined maximum as determined by the g force load to provide an increased volume of breathable $O_2$ to the pilot's lungs. The exhalation and inhalation valves are opened and closed, respectively, during the exhalation phase while the pressure in the inlet/outlet port is allowed to fall from the predetermined maximum to the predetermined minimum. The minimum pressure having a value less than the maximum for g-forces in excess of a selected value, e.g., 2.5–4 g's,. Preferably the maximum pressure is within a range of about 7 to 10 inches of water at about a 2.5 g force and within a range of about 20 to 30 inches of water at about a 9 g force. The minimum pressure is preferably within a range of about 12 to 18 inches of water less than the maximum pressure for g-loads above about 4 g's. The invention may employ a pneumatic system for controlling the functions (i.e., opening/closing) of the inhalation and exhalation valves as well as controlling the maximum and minimum pressures pursuant to a g-force sensor. Alternatively the invention may employ electrically operated variable flow (pressure) inhalation and exhalation valves responsive to the fluid flow path in the inlet/outlet port and the g force load as detected, for example, by a conventional electronic accelerometer. Optionally, the pressure of the gas supplied to the anti-g suit is nonlinear with respect to the g load over the anticipated g load range, e.g., the rate of pressure increase in the anti-g suit is higher during acceleration from low g loads to intermediate g loads and lower during acceleration from intermediate to high g-loads.

The present invention serves to maintain the parameters of a pilot's circulation system in a permissible range for high g-forces thereby enabling the pilot to tolerate such g forces for extended periods with less stress. The present invention also enables a pilot to achieve improved performance while requiring considerably less rehabilitation time after flight as compared with the use of state of the art equipment.

The construction and operation of the present invention may be best understood in reference to the following description taken in conjunction with the accompanying drawings wherein like components are given the same reference number.

DESCRIPTION OF THE PREFERRED EMBODIMENT

The Pressure Regulating Pneumatic Valve Assembly

Figure 5:
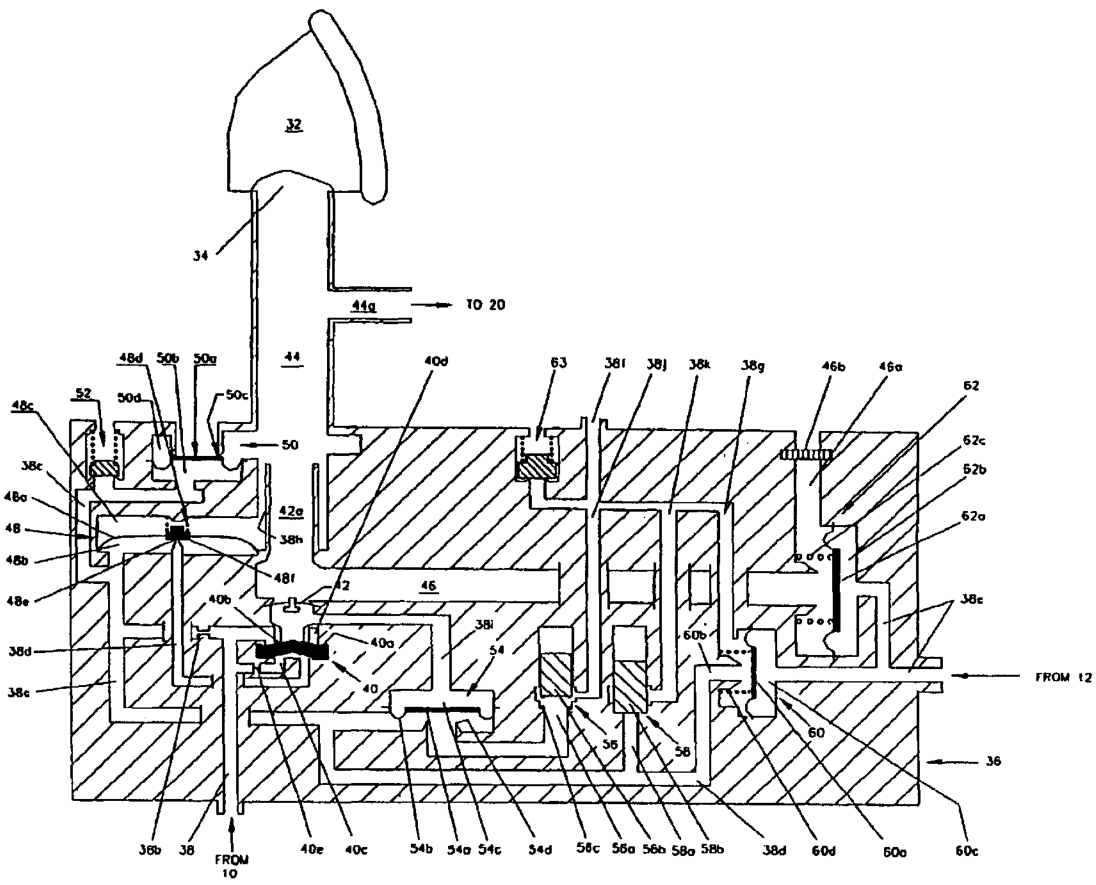
FIG. 5 is a schematic cross-sectional view of a pneumatic valve assembly in accordance with the present invention for controlling the ingress and egress of breathable gas to a pilot's face mask with the inhalation and exhalation valves shown in their closed positions.

Referring now to FIG. 5 a face mask 32, covering the pilot's nose and mouth area, includes an inlet/outlet port 34 which receives $O_2$ from the pressurized source 10 via a valve block assembly 36. The valve block 36 includes a high pressure duct or line 38 adapted to be connected to the source 10, an inhalation check valve 40, which controls the flow of $O_2$ into the mask via a nozzle 42, a diffuser section

42*a* and an outlet 44 connected to the mask inlet/outlet port 34 and to the chest bladder 20 via port 44*a*. The nozzle 42 and diffuser 42*a* form an eductor for drawing in cabin air into the $O_2$ stream entering the mask via duct 46 where the g-force load does not exceed a preselected limit, as will be explained. The inhalation valve 40 includes a flexible diaphragm 40*a* which engages an annular seat 40*b* in the closed position, a lower chamber 40*c* and an upper chamber 40*d*. As illustrated, both the upper and lower chambers are connected to the high pressure duct with a restricted orifice in 38*d* located in the portion of the high pressure line leading to the lower chamber 48*b*. The lower chamber is also connected via pressure relief line 38*b* to a discharge orifice 48*e* of a second diaphragm valve 48 which functions to sense the direction of fluid flow in the inlet/outlet port 34 and thereby the initiation of the pilot's inhalation mode as will be explained. The valve 48 includes a flexible diaphragm 48*a*, a lower chamber 48*b* connected to the high pressure line 38 via a restricted orifice 38*b* and an upper chamber 48*c* connected to the mask inlet/outlet port 34 via passageway 38*h* as illustrated. A spring 48*d* normally biases the membrane 48*a* and its centrally disposed valve member 48*f* against the seat surrounding the orifice 48*e*.

The lower chamber of the flow sensing valve 48 is also connected to a lower chamber 50*b* of an exhalation valve 50 via duct 38*c*. The exhalation valve (shown in its closed position) when open connects the mask inlet/outlet port to a low pressure region such as the aircraft cabin. The valve 50 includes a flexible diaphragm 50*a* which engages, in its closed position, an annular seat 50*c*. The exhalation valve also includes an upper chamber 50*d* in fluid communication with the inlet/outlet port 34. As will be explained in more detail, when the pressure in the upper chamber exceeds the pressure in the lower chamber 50*b* by a sufficient amount to overcome the differences in the areas of the diaphragm 50*a* which are exposed to the upper and lower chambers the valve 50 will open and allow the pilot to exhale.

Figure 1:
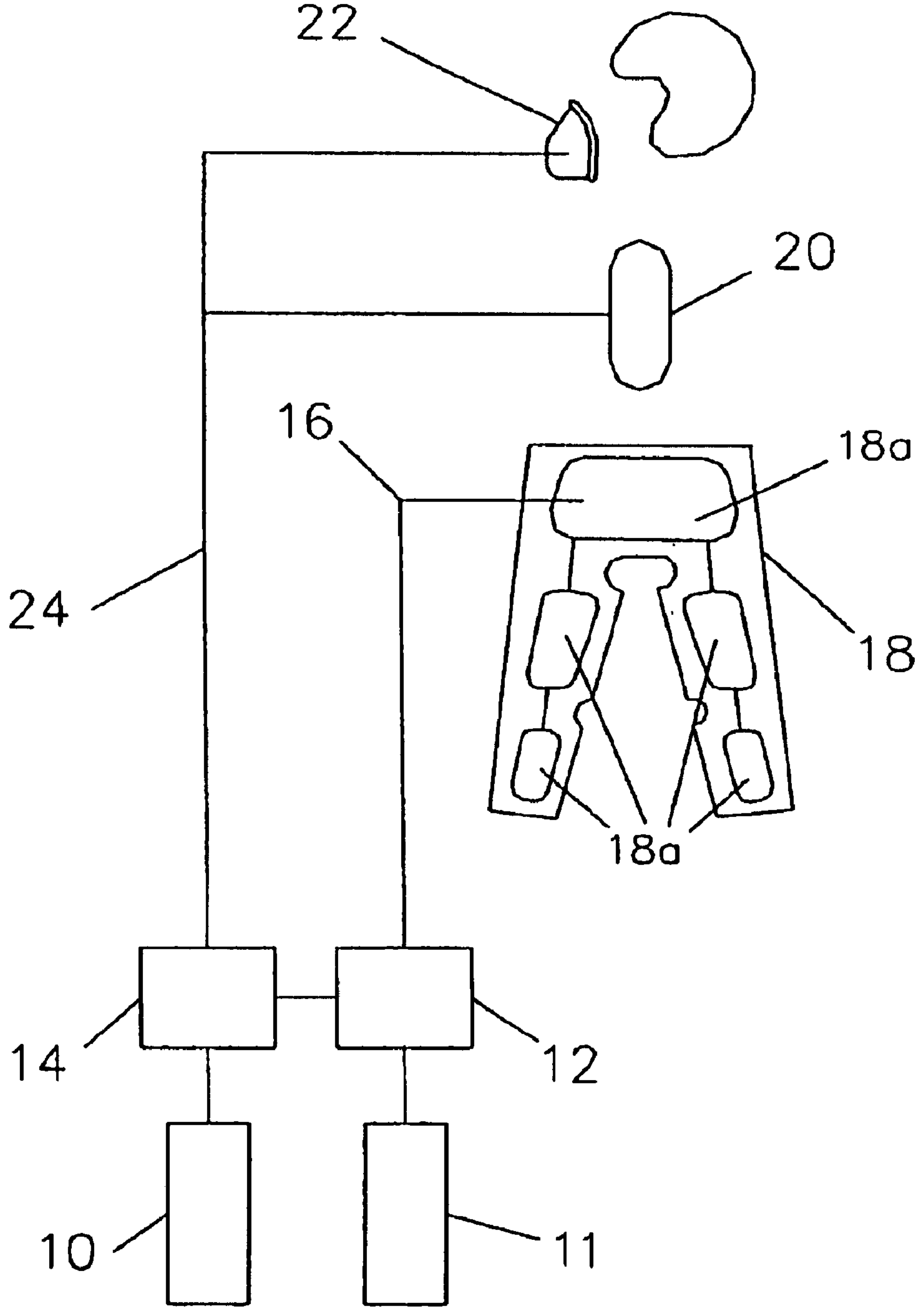
FIG. 1 is a diagram of a conventional anti-g apparatus for use by combat and test pilots.

The lower chamber 50*b* of the exhalation valve 50 is also connected, via duct 38*c* to a safety (poppit) valve 52 which sets a limit to the maximum inhalation pressure. In addition, the lower chamber 48*b* is connected, via a continuation of duct 38*c*, to (a) the lower chamber 54*b* of a normally open diaphragm valve 54 which senses the operation of the inhalation valve, (b) the inlet 56*a* of a minimum inhalation pressure setting valve 56; (c) the inlet 58*a* of a maximum inhalation pressure setting valve 58, via duct 38*d*, and (d) the inlet 60*b* of a cabin vent diaphragm valve 60. A sixth diaphragm valve 62 (when open as shown) connects the passage 46 to the cabin interior via vent port 46*a* and filter 46*b*. The lower chambers 60*c* and 62*b* of the valves 60 and 62, respectively are in fluid communication with the anti-g pressure regulator 12 (FIG. 1) via duct 38*e* so that when the gas from the regulator 12 reaches a predetermined limit, representing a gravitational force of say 2.5 g's, the diaphragms 60*a* and 62*a* will overcome the force of bias springs 60*d* and 62*c* and engage their respective annular seats to close off the inlet 60*b* to the cabin vent port 38*f* via line 38*g* and also close off the duct 46 from the cabin interior thereby stopping the flow of cabin air into the eductor and mask.

Conventional poppit valve 63 serves as a safety valve to vent the duct 38*g* (and ducts 38*j* and 38*k*) to the cabin interior in the event that vent port 38*f* becomes plugged. The remaining parts of valves 54, 56 and 58 will be described in conjunction with the following explanation of the operation of the pressure regulating valve block assembly 36.

Operation of the Pressure Regulating Valve Assembly Without Compensation for High-g Loads In the absence of high g-force loads (e.g., below 2.5 g's) the pressurized $O_2$ in the inlet duct 38 creates (almost immediately after connection to the supply 10) an equal pressure in the lower and upper chambers 40*c* and 40*d* of the inhalation valve 40. As a result of the differences in the surface areas of the diaphragm 50 which are exposed to the two chambers, the inhalation valve is closed as shown in FIG. 5. At the same time $O_2$ flows, via restriction 38*b*, ducts 38*c*, 38*d*, open valve 60 and vent port 38*f* to the low pressure region of the cabin (or atmosphere).

The restriction 38*b* determines the net flow of $O_2$ to the cabin interior for functional purposes. This net flow may be of the order of about 0.5 liters per minute (L/min). At the same time the anti-g regulator pressure/valve 12 (FIG. 1) provides a preliminary filling of the anti-g suit's bladders 18*a* by supplying gas (such as $O_2$) thereto at a positive pressure of say 6–8 inches of $H_2O$.

When the pilot starts to inhale (i.e., initiation of the inhalation phase) a low pressure is created under the mask and in the inlet/outlet port 34 thereof and at the outlet 44 of the valve block assembly 36. This low pressure is transmitted to the upper chamber 48*c*, via duct 38*h*, causing the membrane 48*a* to overcome the bias of spring 48*d* and lift off of the seat surrounding the orifice 48*e*. As a result the pressure in the upper chamber 40*c* of the inhalation valve 40 is rapidly reduced. Since the gas $O_2$ flow through the restriction 40*e* is a considerably less than the gas flow through the open orifice 48*e* (by design) the difference in pressure between the upper and lower chambers will cause the inhalation valve 40 to open. The resulting $O_2$ flow through the nozzle 42 creates a low pressure on the downstream side of the nozzle thereby educting cabin air, via duct 46, open valve 62, duct 46*a* and filter 46*b* into the gas stream exiting the nozzle in a conventional manner. It should be noted that where the aircraft is provided with an on board oxygen generator ("OBOG"), which employs outside air to provide an enriched $O_2$ mixture in lieu of a pressurized $O_2$ container the passage 46 and valve 62 may be eliminated.

The opening of the inhalation valve also creates a high pressure on the upstream side of the nozzle 42 and in the upper chamber 54*c* of the valve 54 (via duct 38*i*) causing the diaphragm 54*a* to engage seat 54*d* and close passage 38*c* from valve 56 and vent 38*f*. This action does not affect the operation of the regulating valve assembly in the absence of a g-force overload (e.g., in excess of 2.5 g's) since passage 38*d* and open valve 60 serve as a bypass to vent duct 38*c* to the low pressure region of the cabin as illustrated.

At the completion of the inhalation phase the low pressure in the upper chamber 48*c* of the inhalation sensing valve 48 declines to say zero (i.e., rises to about cabin pressure) and the spring 48*d* biases the diaphragm 48*a* to again close the orifice 48*e* thereby allowing the pressure in the lower chamber 40*d* of the inhalation valve to increase and force the diaphragm 40*a* to engage its seat 40*b*. This action closes valve 40, terminating the inhalation phase. The valve 54, which senses the cessation of fluid flow through the nozzle also opens as a result of the pressure in the upper and lower chambers equalizing, but without consequence in the absence of a g-force overload. At the initiation of the exhalation phase the pressure in the inlet/outlet port 34 increases to a level slightly above the cabin pressure (due to pilot's exhalation) forcing the diaphragm 50*a* away from its seat 50*c* and exhausting the exhaled air to the cabin. It should be noted that the exhalation phase as used herein means the time period that the inhalation valve remains closed even though a pilot may not commence exhaling gas at the instant of the inhalation valve closure.

Operation of the Pressure Regulating Valve Assembly with Compensation for High g-force Loads When the system is subjected to a predetermined g-force overload, say 2.5 g's, the gas pressure in duct 38*e* (from the anti-g pressure/regulator valve 12) closes valve 62 to cutoff cabin air as a supplement to the $O_2$ from source 10. This same increased pressure closes valve 60 to cutoff passage 38*g* as a bypass to valves 58 and 54 thereby setting up the possibility of creating positive maximum and minimum pressures in the mask inlet/outlet port 34 as well as in the chest bladder via port 44*a* during the inhalation and exhalation phases. It should be noted that valves 60 and 62 need not be arranged to close in response to the same pressure.

Figure 6:
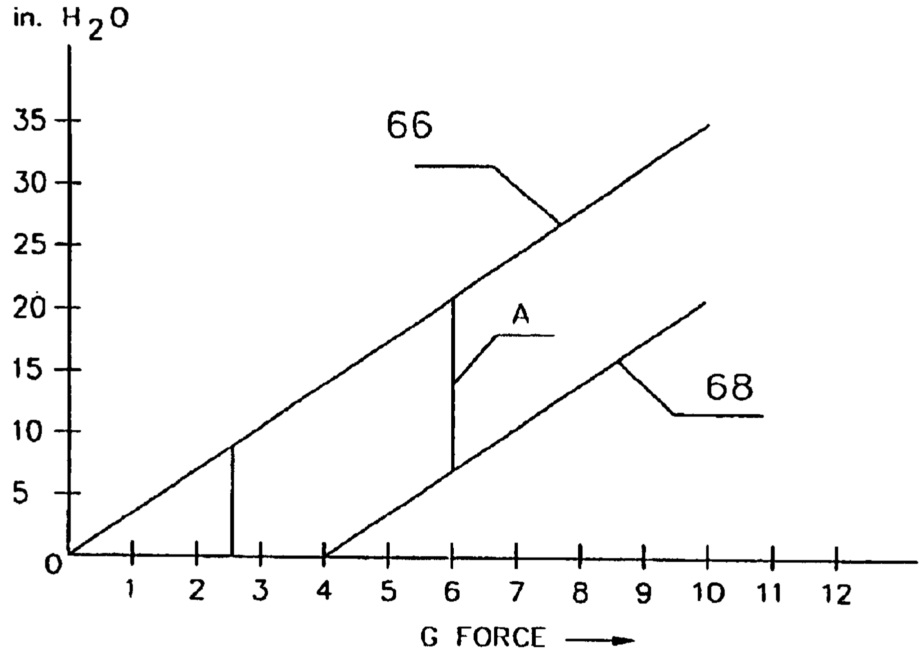
FIG. 6 is a graph showing, as an example, a maximum and minimum pressure as supplied to the inlet/outlet port of the mask of FIG. 5 and chest bladder in inches of $H_2O$ versus g forces.

Curves 66 and 68 of FIG. 6 represent selected values for the maximum and minimum pressures, respectively, for g-force loads above 2.5 g's. While, as is illustrated in the figure, the curves 66 and 68 are linear for g-forces above 2.5 to 4.0 g's, respectively, the curves need not be linear.

As a result of the closure of valve 60 gas within passage 38*c* can be vented to the cabin interior only via g-sensing elements 56*b* and 58*b* (of valves 56 and 58) which close their respective valve inlets 56*a* and 58*a* in response to preselected g-force loads. The g-sensing elements may be in the form of cylindrically shaped weights slidably mounted in cylindrical cavities as illustrated and oriented in a conventional manner to respond to the gravitational forces to which the pilot is being subjected. The g-sensing element 58*b* defines the maximum positive inhalation pressure and g-sensing element 56*b* defines the minimum positive pressure in the mask inlet/outlet port 34.

During exhalation under a preselected g-force load, say 2.5 to 4.0 g's, no positive pressure is created in the mask inlet/outlet port 34, because the diaphragm valve 54 remains open and the spring 56*c* is arranged to prevent element 56*b* from closing inlet 56*a* and interrupting the flow of gas through ducts 38*c* and 38*j* to the cabin vent port 38*f*.

Figure 7:
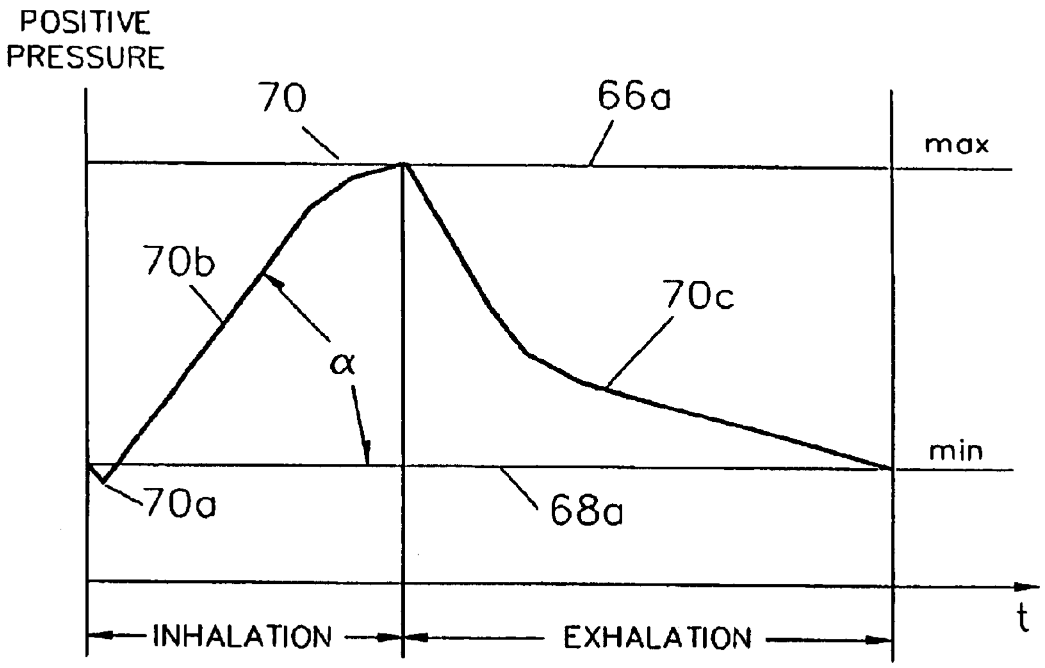
FIG. 7 is a graph of a typical breathing cycle of a pilot employing the apparatus of this invention with the maximum and minimum pressures, of FIG. 6, imposed in the mask inlet/outlet port.

During this same g-force range, the inhalation phase is initiated when the pressure in the mask inlet/outlet port 34 falls to a sufficiently low pressure, say 0.2 to 0.25 inches $H_2O$, to overcome the bias of spring 48*d* and open inhalation valve 40. This low pressure, which is the same as that required without g-force compensation, may be referred to as the threshold of sensitivity. See FIG. 7 and particularly point 70*a* on curve 70 representing a pilot's inhalation and exhalation phases under g-force loads requiring face mask and chest bladder pressure compensation. In this particular case, i.e., g force loads less than a preselected value, say 4 g's, the minimum pressure (68*a* on FIG. 7) would essentially be equal to the cabin pressure.

As discussed above, the opening of the valve 40 creates a positive pressure in the upper chamber 54*c* of the valve 54, thereby closing the valve and cutting off the access of passage 38*c* to the inlet 56*a* of valve 56 and the cabin vent port 38*f*.

At this time a positive pressure is instantly created in the passage 38*c*. This pressure will rise until it reaches a value sufficient to overcome the resistance of the g-sensing element 58*b*. At that point in time $O_2$ will flow through the valve 58, the passage 38*k* and then to the cabin via vent port 38*f*. This pressure corresponds to the maximum positive pressure, which will be created in the mask inlet/outlet port 34 g) and in the chest bladder at the end of the inhalation phase. This positive pressure is transmitted to the lower chamber 48*b* of the valve 48 and maintains the inhalation valve 40 open until the pressure in the upper chamber 48*c* achieves the same value and allows the spring 48*d* to close valve 48 with the consequence that the inhalation valve is also closed terminating the inhalation phase. Curve segment 70*b* represents the positive pressure buildup in the inlet/outlet port 34 and the chest bladder during the inhalation phase. This same positive pressure exists in the lower and upper chambers 50*b* and 50*c* of the exhalation valve 50.

Once the inhalation valve closes the pressure in the upper and lower chambers 54*d* and 54*b* equalize and allow the valve to open thereby venting passage 38*c* to the cabin via open g-sensing valve 56, duct 38*j* and vent port 38*f*.

Figure 4:
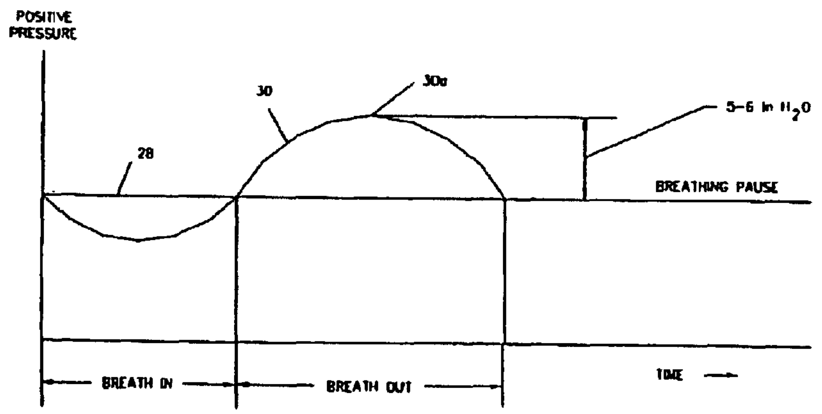
FIG. 4 is a graph illustrating a pilot's typical breathing cycle when using the equipment of FIG. 1 with a positive pressure supplied to the mask to compensate for a high g force.

The pressure in the lower chambers 48*b* and 50*b* of valves 48 and 50 also rapidly decline due to the venting of passage 38*c*, opening the exhalation valve 50 to exhaust the pilot's exhaled air. When the g-force is greater than the selected 4 g's, this pressure declines to a value defined by the resistance of g-sensing element 56*b*. The pressure, for example, at about 7 g's, may be of the order of about 10 inches $H_2O$ as is illustrated by FIG. 6. Again, as the pressure in the lower chamber 50*b* of the exhalation valve 50 decreases to the minimum level 68*a* (FIG. 7) the exhalation valve opens and gas is released from the pilot's lungs to the cabin with a minimum effort on the part of the pilot. Compare, for example, FIGS. 4 and 7. It should be noted that the pressure rise gradient, i.e., represented by the angle $\alpha$ in FIG. 7, should (a) be sufficient to provide the necessary maximum pressure in the lungs during a reasonable inhalation time frame and (b) not exceed a rate (maximum value) which would possibly injure the tender lung tissues. As an example, the maximum pressure should preferably not be reached during the initial three-fourths of the inhalation phase.

Test Results

Tests of the invention were made by subjecting healthy men, in good physical condition, to the g forces indicated via a centrifuge while the men were equipped with conventional anti-g force protection apparatus and with the apparatus of the present invention. The pressure differential (i.e., max vs. min) used was about 16 inches $H_2O$. The individuals performance efficiency was evaluated on the basis of the impairment of their periphery vision angle. An individual's performance capability was considered to be compromised when his peripheral vision became limited to 70°.

The maximum inhalation pressure represented by curve 66 in FIG. 6 may be about the same that was provided by the state of the art anti-g systems relying on the same pressure in the mask for any given g-force load. The minimum exhalation pressure represented by curve 68 in FIG. 6 is preferably within the range of about 14 to 20 and most preferably about 16 to 18 inches of $H_2O$ less than the maximum inhalation pressure for all g-force loads above a selected minimum, say about 4 g's.

Figure 8A:
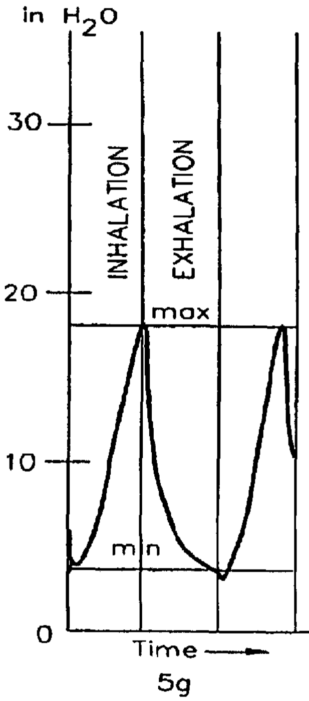
FIGS. 8 *a, b*, and *c* are graphs showing the actual breathing cycles of an individual employing the apparatus of this invention at g-forces of 5, 7, and 9, respectively.
Figure 8B:
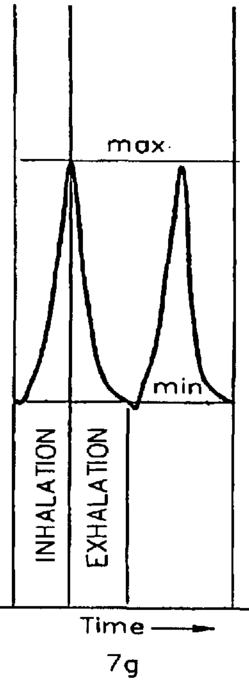
Figure 8C:
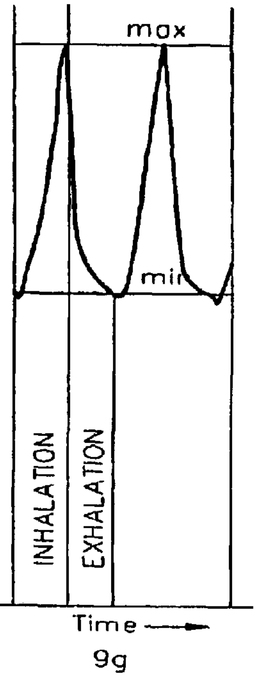

The graphs of FIGS. 8*a*,8*b*, and 8*c* depict the actual breathing cycle of an individual undergoing a test while equipped with the present invention. The graphs, which are self-explanatory, illustrate the rise and fall of the mask inlet/outlet port pressure during the inhalation and exhalation phases when the individual was subjected to the noted g-force loads. These graphs all depict the actual maximum and minimum pressures with a difference thereof of about 16 inches $H_2O$.

Figure 9A:
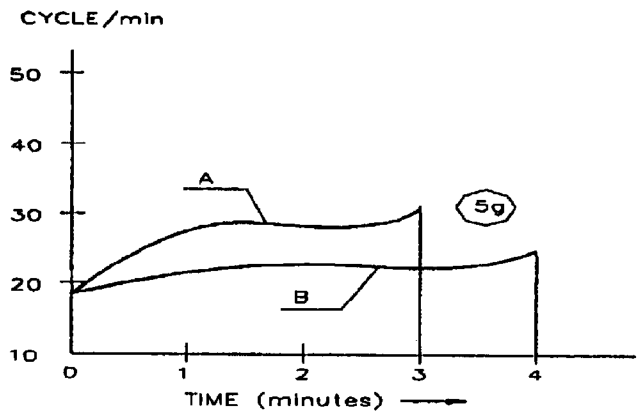
FIGS. 9 *a, b*, and *c* are graphs of waveforms illustrating a typical breathing rate in breaths/minute of an individual using conventional anti-g equipment (curve A) versus using the present invention (curve B) at g-forces of 5, 7, and 9, respectively.
Figure 9B:
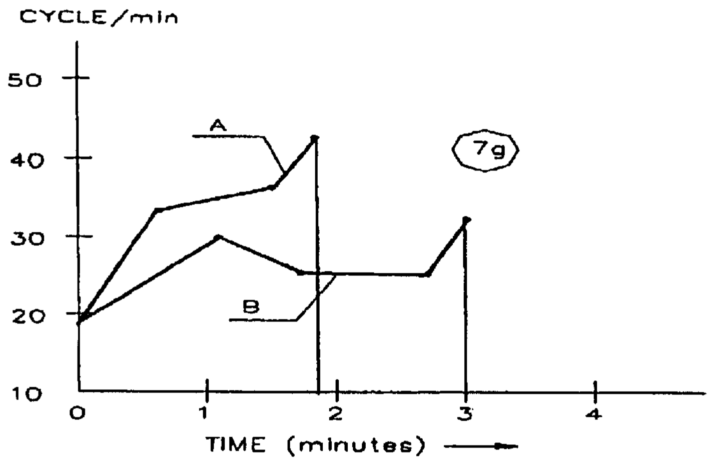
Figure 9C:
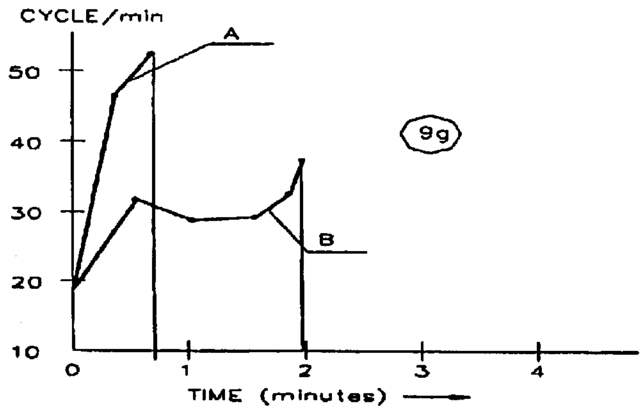

The graphs of FIGS. 9*a*, 9*b* and 9*c* illustrate the typical breathing rate in cycles/minutes of an individual undergoing tests at 5, 7, and 9 g-forces using conventional anti-g equipment (curve A) and the present invention (curve B).

Figure 10A:
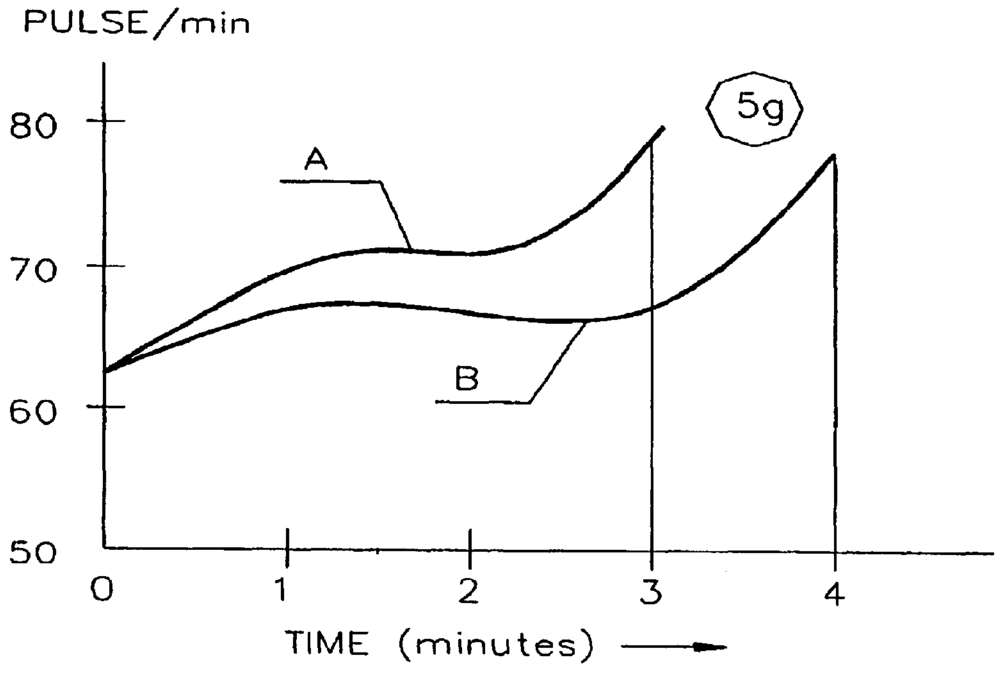
FIGS. 10 *a, b*, and *c* are graphs showing the typical pulse rate of an individual using conventional anti-g equipment (curve A) versus using the present invention (curve B) at g-forces of 5, 7, and 9, respectively.
Figure 10B:
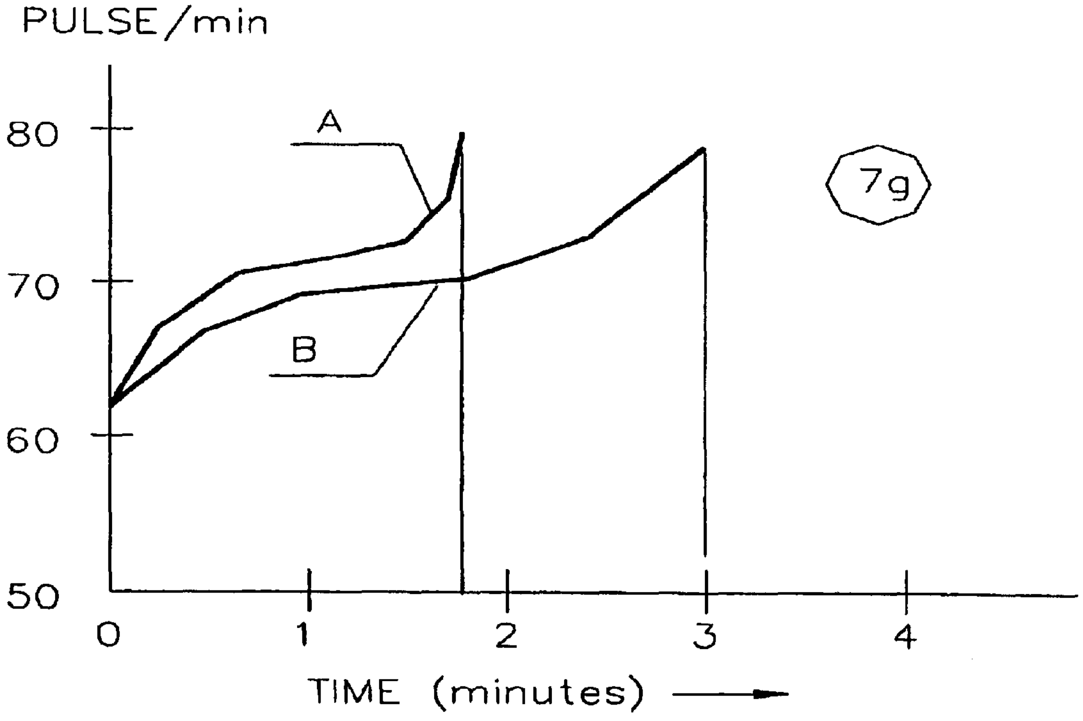
Figure 10C:
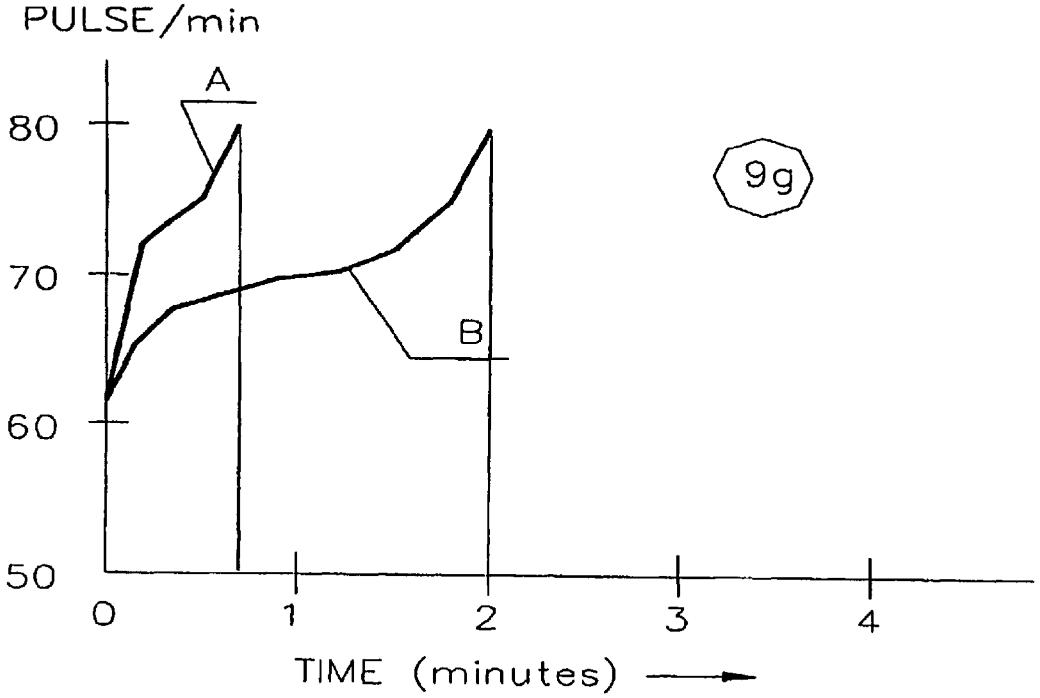
Figure 11A:
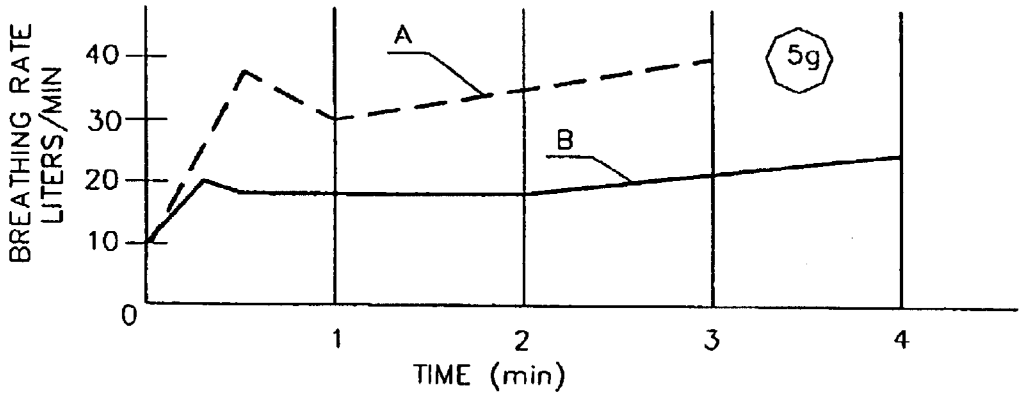
FIGS. 11 *a, b*, and *c* are graphs showing the typical lung ventilation rate of an individual using conventional anti-g equipment (curve A) versus using the present invention (curve B) at g-forces 5, 7, and 9, respectively.
Figure 11B:
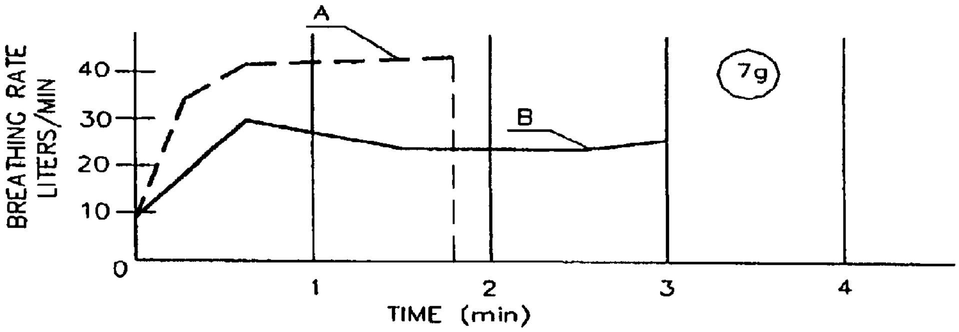
Figure 11C:
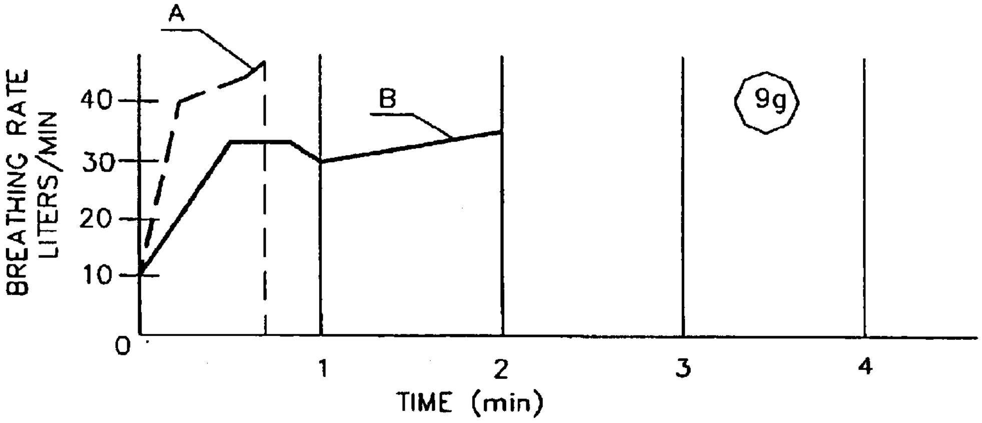

The graphs of FIGS. 10*a*, 10*b*, and 10*c* represent an individual's pulse rate at 5, 7 and 9 g-forces using conventional anti-g equipment (curve A) and the present invention (curve B). The graphs of FIGS. 11*a*, 11*b* and 11*c* represent an individual's ventilation rate in liters/min at 5, 7, and 9 g-forces using conventional anti-g equipment (curve A) and the present invention (curve B). The tests of FIGS. 9, 10 and 11 were terminated when the test individual performance capability was compromised as discussed earlier.

The tests results of FIGS. 9 and 10 show that an individual's breathing and heart rate was overloaded considerably when equipped with the state of the art system and remarkably so at 9 g's in contrast to the use of the present invention. The ventilation rate was also considerably higher when using conventional equipment versus the invention as is illustrated in FIG. 11. The duration of satisfactory tolerance time also increased with the invention versus the state of the art equipment. Also, the individuals undergoing the tests with the invention were able to have two-way radio communications.

The maximum pressure gradient α (FIG. 7) during inhalation initially set at 28 inches of $H_2O$/sec. was reduced to 25 inches $H_2O$/sec. to comply with two of the testers complaints that breathing was unpleasant at the higher rate. No complaints were voiced when the rate was reduced.

The test results show that the present invention overcomes many of the short comings of the current state of the art anti-g systems and will enable a pilot to utilize to a much greater extent the performance capabilities of modem aircraft.

The Pressure Regulating Electronic Valve Assembly

Figure 12:
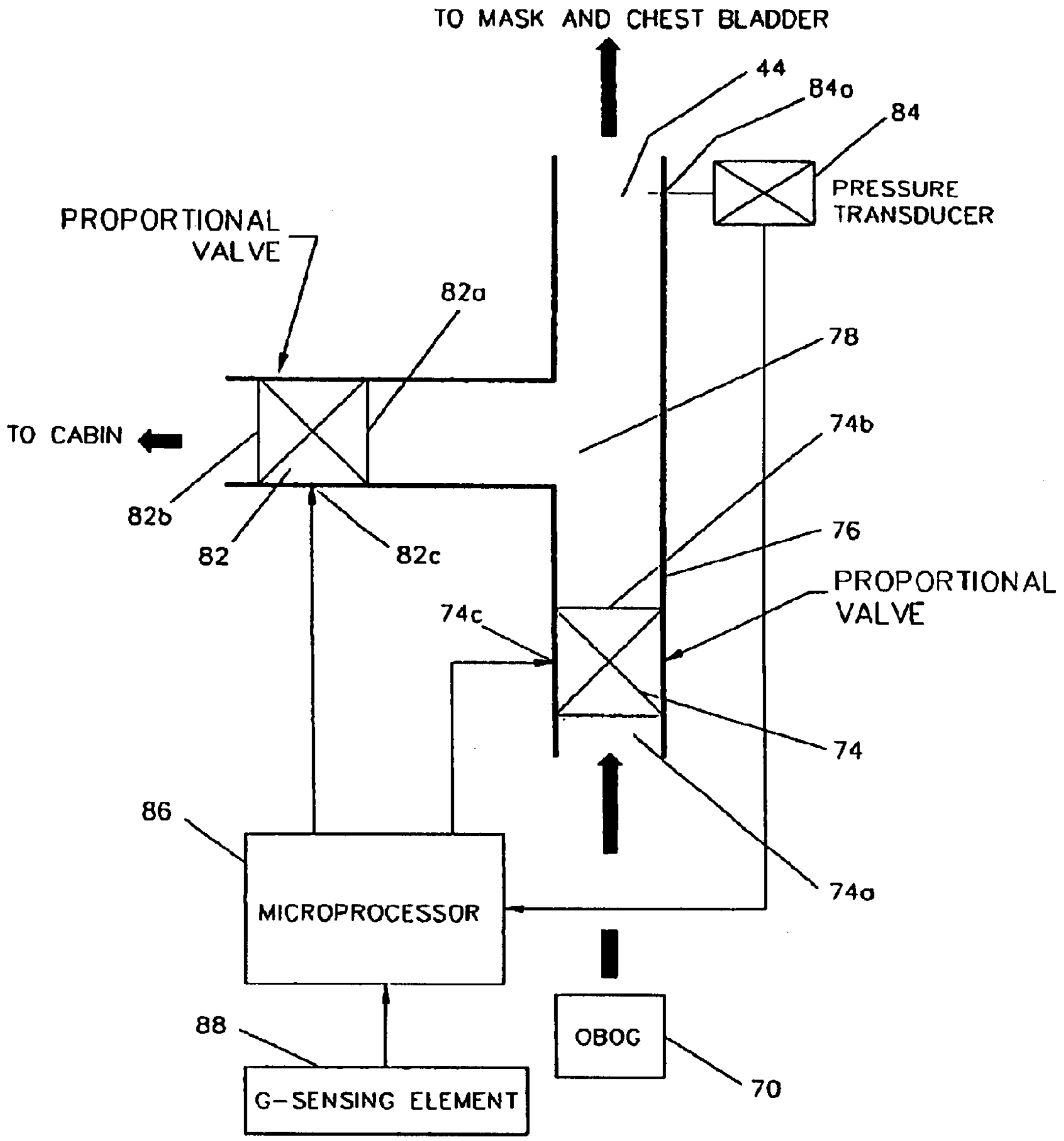
FIG. 12 is a block diagram of an alternative embodiment in the form of an electronic/pneumatic apparatus for controlling the ingress and egress of breathable gas to and from the mask and chest bladder.

An alternative embodiment of the present invention in the form of an electronic/pneumatic valve and pressure regulating system is illustrated in FIG. 12. An on-board oxygen generator ("OBOG") 70 provides pressurized $O_2$ to the inlet 74*a* of an inhalation valve 74 located in a housing 76. The outlet 74*b* of valve 74 is connected to the mask inlet/outlet port 34 via a housing duct 78, and outlet 44. An exhalation valve 82 has an inlet 82*a* connected to the mask inlet/outlet port via outlet 44 and an outlet 82*b* in fluid communication with the cabin or low pressure region. The exhalation valve controls the pressure at which air may be exhaled (to the cabin) by the pilot. A pressure transducer 84 senses the pressure in the outlet 44 (and the mask inlet/outlet port) via probe 84*a* and provides a signal representative of such pressure to a microprocessor or computer 86. A g-sensing element 88, which may be of an electronic accelerometer type, provides a signal to the microprocessor 86 representative of the g-forces to which the pilot is being subjected. The pressure regulating valves 72 and 82 may be of the type in which a solenoid operates a diaphragm to control the magnitude of fluid flow through the valve (and outlet pressure) in accordance with an electric current. One such valve is manufactured by South Bend Controls Inc. of Southbend, Ind. under the part number 27722. Such a valve must be able to accommodate the anticipated high g-forces. The microprocessor is programmed to open and close the valves 74 and 82, respectively, upon the initiation of the inhalation phase via a signal from pressure regulator 84. The microprocessor monitors the pressure and the pressure change in outlet 44 via pressure transducer 84. When the pressure changes in outlet 44 after exhalation by a threshold amount signifying that the pilot has initiated the inhalation phase, the microprocessor applies a signal to input circuit 74*c* to open the valve and adjust the solenoid current, to cause the pressure at 44 to substantially follow the curve 70*b* of FIG. 7. At the same time the microprocessor applies a signal to the input of the exhalation valve 82 to close the same. When the pressure at 44 reaches the selected maximum inhalation pressure for the g-force experienced by the pilot the microprocessor turns off the inhalation valve 74 and opens the exhalation valve 82 via a signal to input circuit 82*c* to commence the discharge of $O_2$ within the duct 78. The microprocessor further controls the minimum pressure at which the exhaled air will be discharged through the valve 82. This process repeats itself to supply $O_2$ to the mask inlet/outlet port from the minimum to the maximum pressure during the inhalation phase and to allow the pressure therein to fall to the minimum pressure during the exhalation phase, thereby greatly decreasing the exhalation effort required by the pilot. It should be noted that a flow sensor may be used to detect the initiation of the inhalation phase in lieu of discerning the change in pressure by the pressure transducer. Since the system of FIG. 11 may be programmed to have a faster response time than the pneumatic system of FIG. 5 the exhalation pressure curve may have a faster decay time. However, the rise time of the inhalation curve is limited by a pressure gradient α (FIG. 7) which will not endanger the pilot's lungs.

Figure 2:
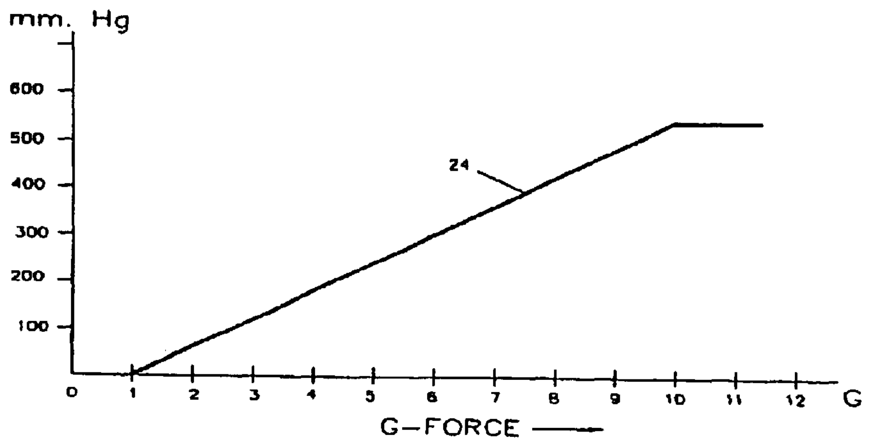
FIG. 2 is a graph illustrating a typical anti-g suit pressure versus g-force for the equipment of FIG. 1.
Figure 3:
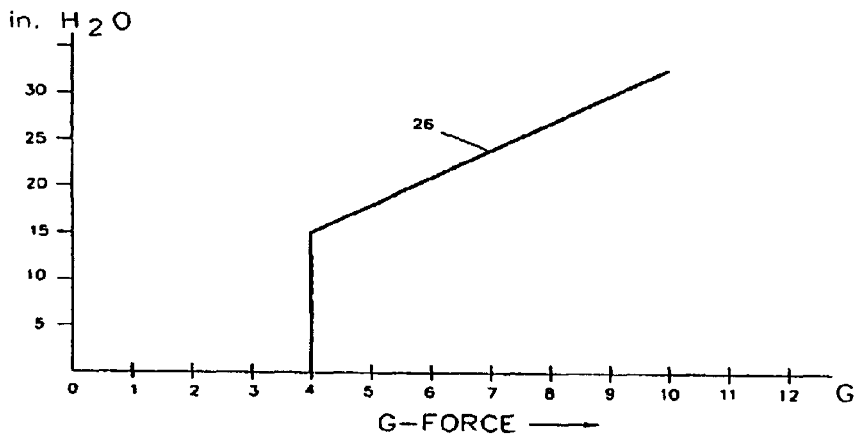
FIG. 3 is a graph illustrating a typical gas supply pressure to the pilot's face mask and chest bladder versus g-force for the equipment of FIG. 1.

Optional Nonlinear G-responsive Pressure Regulator for Supplying Pressurized Gas to the Anti-g suit Current anti-g valves for use in high performance aircraft provide an output pressure schedule that is linear with increasing gravity forces. A typical schedule is shown as curve 24 in FIG. 2. There is evidence that an optimal schedule would more nearly follow a non-linear curve depicted by curve 92 in FIG. 13.

Such a curve can be implemented through the use of a proportional valve 74 (FIG. 12) in conjunction with a g-sensing element 88 and a controller or microprocessor 86 wherein the flow rate (and outlet pressure) through the valve 74 is controlled via appropriate programming of the microprocessor. It is to be noted that the inlet proportional valve 74 would be connected to a source of pressurized gas from an engine driven compressor, for example, and the outlet would be connected to the anti-g suit bladders.

Figure 13:
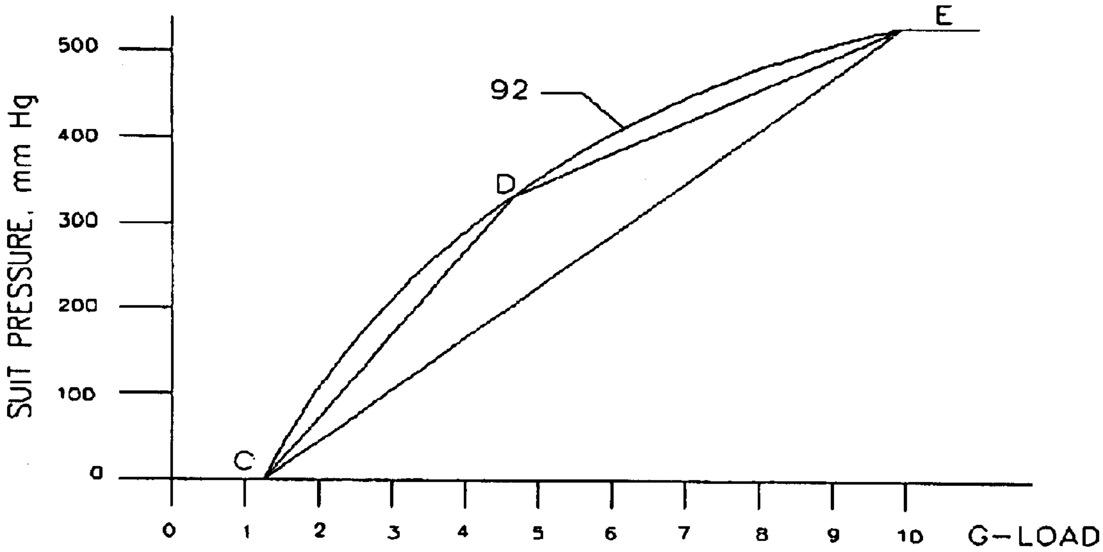
FIG. 13 is a graph illustrating an optimal schedule of anti-g suit pressure with increasing gravity forces and an approximation of such schedule using a regulator in accordance with the invention.

A single pneumatic pressure responsive regulator for providing pressure regulation characteristics which approximates the curve 92, i.e., that follow two intersecting lines, such as shown by curve CDE, is illustrated in FIG. 13 wherein a flow control valve 94 controls the flow of gas from the pressurized gas source 11 (e.g., 1.5 to 10 Bars) to an anti-g suit (FIG. 1) via inlet passage 96 and outlet port 98. The pressure schedule which simulates a nonlinear curve, e.g., curve 92 through the use of a plurality of straight intersecting line segments over the anticipated g-load range, e.g., C D and D E is also referred to herein as nonlinear.

The control valve 100 includes a diaphragm 100*a* disposed between upper and lower chambers 110*b* and 100*c*, respectively. Chamber 100*b* receives pressurized gas from the inlet 96 via restrictor 96*a* with no g-load present. The valve 100 is closed, i.e., diaphragm 100*a* seats against seat 100 as a result of the diaphragm having a greater area exposed to the upper versus the lower chamber. Gas also flows through restrictor 96*b* along channel 96*c* into an upper (reference pressure) chamber 102*b* of a second diaphragm valve 102 and then through the seat 104*a* of a first g-load sensing element 104 which element is biased into its open position via spring 104*b*. The gas, after passing through seat 104*a*, flows through chamber 106, channel 108, normally open test valve 110, channel 108*a* and finally to the inlet 112*a* of valve 112, biased to its closed position via spring 112*b*.

Valve 112 creates a small positive pressure, e.g., 4 to 8 inches of water, in upper chamber 102*b* that will cause the diaphragm 102a to move against pilot valve 114. This will cause gas to flow from the upper chamber 100b of the control valve 100 through the pilot valve seat 114a and through channel 98a to the outlet port 98 and the anti-g suit connected thereto. This flow will result in a drop in pressure in the upper chamber 100b due to the action of the flow restrictor 96a which in turn causes the diaphragm 100a to lift off its seat and open the flow control valve 100 and allow gas to flow through the outlet port until the pressure in the outlet port is equal to the pressure in upper chamber 102b of diaphragm valve 102. At this time, the diaphragm 102a moves away from the pilot valve 114, allowing the spring 114a to close the valve 114. At this same time the pressure in upper chamber 100b equals the supply pressure from source 11 and the flow control valve shuts off flow to the outlet port 96. This initial operation creates a constant positive pressure in the anti-g suit bladders for initial filling. The pressure in a lower chamber 116c of a third diaphragm valve 116 is transmitted from upper chamber 102b through channel 96c and acts to open or close diaphragm valve 116 and flow therethrough to the outlet port so as to maintain the pressure in outlet port 96 approximately equal to the pressure in the upper chamber 102b.

Figure 14:
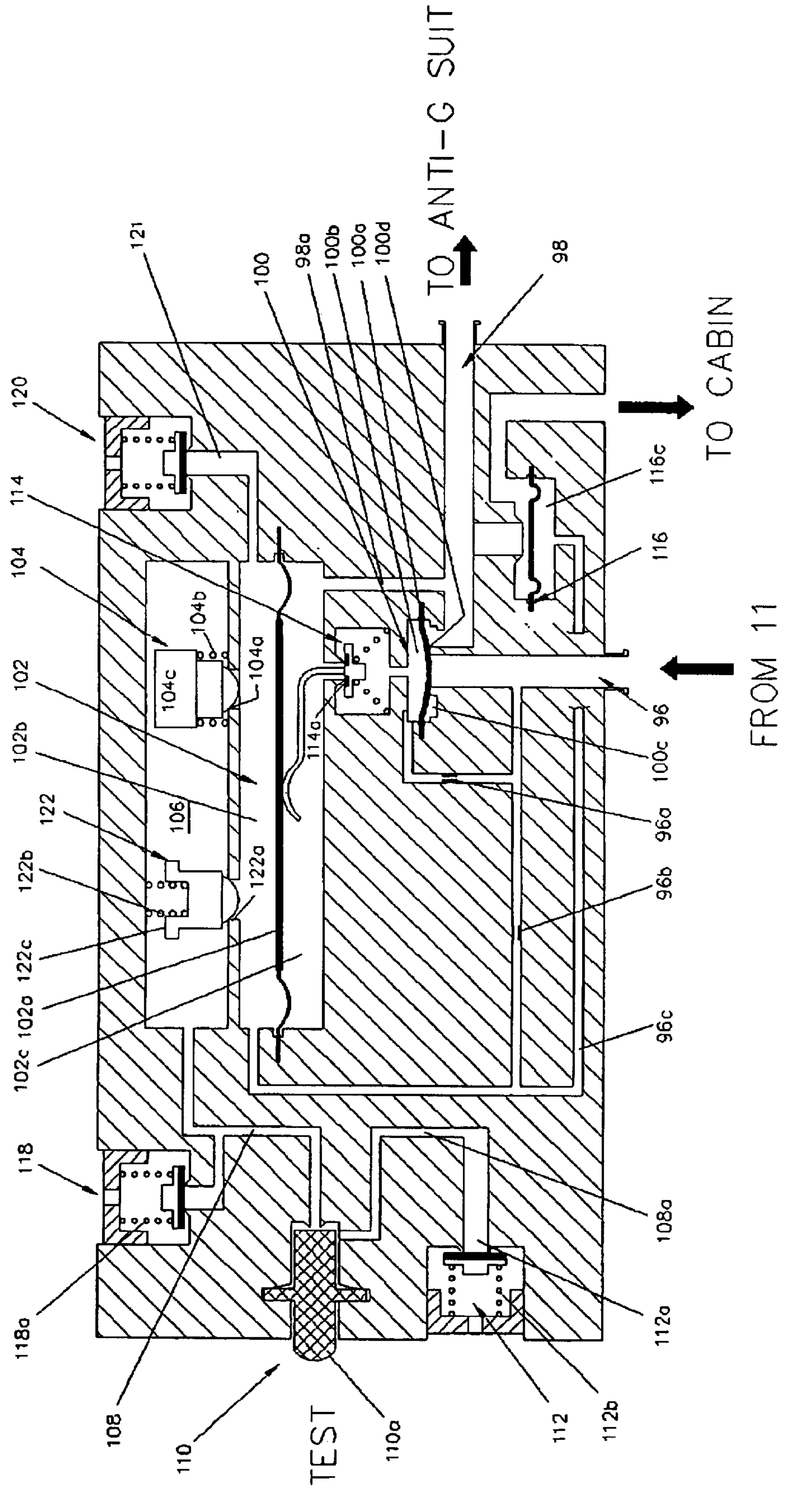
FIG. 14 is a diagrammatic diagram of a pneumatic pressure regulator for supplying pressure to a pilot's anti-g suit.

In order to check the performance of the g-responsive pressure regulator assembly of FIG. 14, the pilot presses the test button 110a which closes the flow through channel 108a. Spring biased relief valve 118 then acts to control the pressure in upper chamber 102b. Valve 118 is typically set to open, via spring 118a, at a pressure of 10 to 12 inches of water. A second spring biased relief valve 120 connected to the upper chamber 102b through channel 121 acts, via spring 120a, to limit the pressure in the upper chamber and thus the outlet pressure to a safe maximum level.

Two g-load sensors, i.e., 104 and 122 are connected in parallel to control the reference pressure in upper chamber 102b. Sensor 104 consisting of weight 104c and spring 104b produces a pressure schedule as shown by curve C F in FIG. 15. Sensor 122, via weight 122c and spring 122b produces a pressure schedule as shown by curve G E, i.e., gas will flow through its inlet 122a when the pressure in the upper chamber 102b is sufficient to lift the weight as biased downwardly by spring 122b, off of its seat 122a. The resulting reference pressure in chamber 102b (and in the outlet 99) will be the lessor of the two schedules as shown by curve C D E in FIG. 15. The chamber 106 is sometimes hereinafter referred to as a low pressure region.

Figure 15:
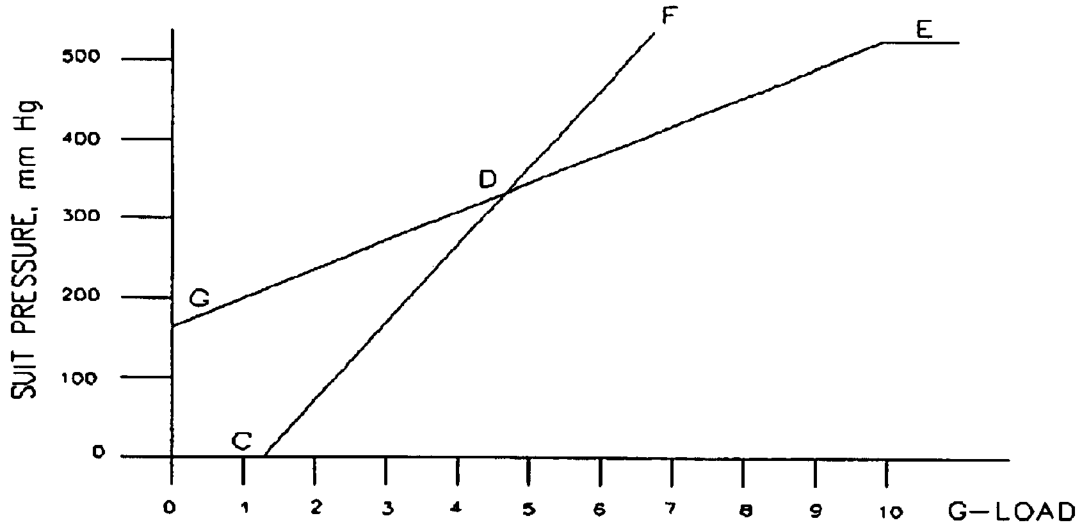
FIG. 15 is a graph illustrating the operation of the two g-load sensors incorporated into the regulator of FIG. 14.

It is to be noted that rate of pressure increase in the anti-g suit is higher during acceleration from low g loads to intermediate g loads, i.e., from C to D in FIG. 15 and at a lower rate during acceleration from intermediate g loads to high g loads, i.e., D to E in FIG. 15.

There has been described a novel method and apparatus for regulating the inhalation and exhalation of breathable gas, such as $O_2$ or a mixture of $O_2$ and air, to and from a pilot's lungs while the pilot is equipped with an anti-g force suit, a face mask with a common inlet/outlet port and an inflatable chest bladder during high-g maneuvers. Optionally the anti-g suit may be inflated at a nonlinear pressure schedule. The invention greatly reduces the stress imposed on a pilot when breathing at high g-force loads thereby enabling the pilot to comfortably withstand high g-force loads for an extended period. As a result, a pilot can more fully accommodate the high performance characteristics of modern aircraft and space ships. Various modifications of the particular embodiments disclosed herein will become apparent to those skilled in the art without involving any departure from the spirit and scope of the invention as defined by the appended claims.

What is claimed is:

1. A method of regulating the inhalation and exhalation of breathable gas to and from a pilot's airway in response to the pilot's spontaneous inhalation and exhalation breathing phases, while the pilot is experiencing excessive g-forces and equipped with an anti-g force suit and a face mask having a common inlet/outlet port in fluid communication with the pilot's airway comprising:

providing a source of pressurized breathable gas;

providing an inhalation valve connected between the source of pressurized gas and the inlet/outlet port of the face mask;

providing an exhalation valve connected between the inlet/outlet port of the face mask and a low pressure area;

opening and closing the inhalation and exhalation valves, respectively, during the inhalation phase and controlling the pressure of gas supplied to the inlet/outlet port so that the pressure rises from a predetermined minimum to a predetermined maximum to increase the volume of breathable gas supplied to the pilot's lungs; and opening and closing the exhalation and inhalation valves, respectively, during the exhalation phase and controlling the pressure in the inlet/outlet port so that the pressure falls from the predetermined maximum to the predetermined minimum to decrease the exhalation effort required by the pilot, the maximum pressure being a function of the g-forces to which the pilot is being subjected, the minimum pressure having a value less than the maximum for g-forces in excess of a selected value of g-force.

2. The method of claim 1 wherein the predetermined maximum pressure is within a range of about 5 to 12 inches of water at about a 2.5 g-force and is within a range of about 25 to 35 inches of water at about a 9 g-force.

3. The method of claim 1 wherein the predetermined minimum pressure falls within a range of about 10 to 20 inches of water less than the maximum pressure at any g-force greater than about 4.

4. The method of claim 3 wherein the minimum pressure falls within a range of about 14 to 18 inches of water less than the maximum at any g-force greater than about 4.

5. The method of claim 3 wherein the relationship between the maximum pressure and the g-force is approximately linear for g-forces in excess of about 4 to 5 g-force.

6. The method of claim 1 wherein the maximum pressure gradient a during the inhalation phase is within the range of about 20 to 27 inches $H_2O$.

7. The method of claim 6 wherein the pressure gradient a is about 24 inches $H_2O$.

8. The method of claim 1 wherein the pilot is further equipped with an inflatable chest section and further comprising the step of inflating and deflating the chest section in synchronism with the gas supplied to and withdrawn from the face mask.

9. The method of claim 8 wherein the pressure in the chest section is approximately the same as the pressure in the mask inlet/outlet port.

10. The method of claim 1 further including inflating the anti-g suit with gas at a pressure which varies nonlinearly over the anticipated g-force range.

11. The method of claim 10 wherein the pressure in the anti-g suit increases at a higher rate during acceleration from low g loads to intermediate g loads and at a lower rate during acceleration from intermediate g loads to high g loads.

12. A system for controlling the pressures at which breathable gas is spontaneously inhaled from a high pressure source and exhaled to a low pressure region by a pilot while experiencing excessive g-forces and equipped with an anti-g-force suit comprising:

a face mask having a common inlet/outlet port in fluid communication with the pilot's lungs;

an inhalation valve/pressure regulator subsystem having an inlet connected to the high pressure source and an outlet connected to the inlet/outlet port of the face mask, the inhalation valve/pressure regulator subsystem being arranged to connect the high pressure source to the mask inlet/outlet port in response to a pressure in the mask inlet/outlet port falling below a minimum level and to limit the maximum pressure in the mask inlet/outlet port to a maximum level in response to the g-force to which the pilot is being subjected; and an exhalation valve/pressure regulator subsystem having an inlet connected to the inlet/outlet port of the face mask and an outlet connected to a low pressure region, the exhalation valve/pressure regulator subsystem being arranged to connect the mask inlet/outlet port to the low pressure region in response to the pressure in the inlet/outlet port reaching the maximum level and to limit the minimum pressure in the mask inlet/outlet port to the minimum level in response to the g-force to which the pilot is being subjected, with the second level being less than the first level for g-forces greater than a selected value of g-force.

13. The invention of claim 12 wherein the inhalation valve/pressure regulator subsystem includes:

a first g-force sensing valve (58) coupled to the high pressure source for establishing the maximum pressure level representative of the g-force;

a normally closed first diaphragm valve (40) connected between the high pressure source and the mask inlet/outlet port; and a normally closed second diaphragm valve (48) connected to the mask inlet/outlet port and to the first diaphragm valve and responsive to the maximum and minimum pressure levels and the pressure in the mask inlet/outlet port, the second diaphragm valve being arranged to open the first diaphragm valve in response to the pressure in the mask inlet/outlet port falling below the minimum level by a threshold amount and to close the first diaphragm valve in response to the pressure in the mask inlet/outlet port reaching the maximum level.

14. The invention of claim 13 wherein the exhalation valve/pressure regulator subsystem includes:

a second g-sensing valve (56) coupled to the high pressure source for establishing the minimum pressure level representative of the g-force;

a third diaphragm valve (50) connected between the mask inlet/outlet port and the low pressure region; and a fourth diaphragm valve (54) responsive to the condition of the inhalation valve for opening the third diaphragm valve in response to the first diaphragm valve closing and for limiting the fluid flow through the third diaphragm valve so that the pressure in the mask inlet/outlet port does not fall below the minimum level.

15. The invention of claim 12 wherein the inhalation valve/pressure regulator subsystem includes:

an accelerometer (88) for generating an output signal representative of the g-force to which the pilot is subjected;

a pressure transducer (84) coupled to the mask inlet/outlet port for providing an output signal representative of the pressure in the mask inlet/outlet port;

a first proportional valve (74) having an inlet connected to the high pressure source and an outlet connected to the mask inlet/outlet port, the first proportional valve having an input circuit **(74*a*) and being arranged to open or close and control the gas pressure in the outlet thereof when open in accordance with signals applied to its input circuit; and a controller (88)** responsive to the output signals from the accelerometer and the pressure transducer for determining the maximum and minimum pressure signals and for applying signals to the input circuit of the proportional valve to open the first valve when the change in the signal from the pressure transducer signifies that fluid has commenced to flow into the mask inlet/outlet port and to cause the first valve's outlet pressure to rise at a given rate to the maximum pressure and to close the first valve when the maximum pressure is reached.

16. The invention of claim 15 wherein the exhalation valve/pressure regulator subsystem includes:

a second proportional valve (82) having an inlet **(82*a*) connected to the mask inlet/outlet port and an outlet (82*b*) connected to the low pressure region, the second proportional valve having an input circuit (82*c*)** and being arranged to open or close and control the gas pressure in the inlet thereof when open in accordance with signals applied to the input circuit and wherein the microprocessor in response to the accelerometer output signal and the condition of the first proportional valve applies signals to the input circuit of the second proportional valve to open the second valve when the first valve closes and limits the inlet pressure of the second valve to the minimum pressure and to close the second valve upon the opening of the first valve.

17. An apparatus for controlling the pressures at which breathable gas is spontaneously inhaled from a high pressure breathable gas source and exhaled to a low pressure region by a pilot while equipped with an anti-g suit including a pneumatic chest compression section and experiencing excessive g-forces comprising:

a face mask having a common inlet/outlet port in fluid communication with the pilot's lungs and the chest compression section;

a inhalation valve having an inlet connected to the high pressure source and an outlet connected to the mask inlet/outlet port; at least one g-force sensor;

a pressure sensor/regulator connected to the gas source, the inlet/outlet port of the mask and the inhalation valve and being responsive to the g-force sensor for opening the inhalation valve to conduct gas from the gas source to the mask inlet/outlet port during the inhalation mode and for closing the inhalation valve when the pressure in the mask inlet/outlet port reaches a maximum value, the maximum value being a function of the g-force to which the pilot is being subjected;

an exhalation valve connected to the high pressure source, the low pressure region and the mask inlet/outlet port; and a flow sensor/regulator connected to the high pressure source and the inhalation valve outlet and responsive to the g-force sensor for conducting gas from the mask inlet/outlet port to the low pressure region during the exhalation mode while limiting the pressure within the inlet/outlet port to a predetermined minimum value as a function of the g-force, the minimum value being lower than the maximum value for g-forces greater than a selected value of g-force.

18. The apparatus of claim 17 wherein said at least one g-force sensor comprises first and second sensors, the inhalation valve is a diaphragm valve (40) and the pressure sensor/regulator is a diaphragm valve (48) having pressure actuating chambers disposed on upper and lower sides of the diaphragm with the upper chamber **(48*c*) being in fluid communication with the mask inlet/outlet port and the lower chamber (48*b*)** being in fluid communication with the gas source, the inhalation valve and the first g-force sensor, the pressure sensor diaphragm valve further including a bias member for closing the pressure sensor diaphragm valve when the pressure in the upper chamber is equal to or greater than the pressure in the lower chamber and for opening the valve when the pressure in the lower chamber is greater than the pressure in the upper chamber.

19. The apparatus of claim 18 wherein the exhalation valve is a diaphragm valve (50) and the flow sensor/regulator is a diaphragm valve (54) having pressure actuating chambers disposed on upper and lower sides of the diaphragm with the upper chamber **54*c* in fluid communication with the inhalation valve outlet and the lower chamber (54*b*)** in fluid communication with the gas source, the exhalation valve and the second g-force sensor.

20. The apparatus of claim 17 wherein the inhalation valve is an electrically responsive proportional valve (74), the g-force sensor is an accelerometer (88) and the pressure sensor/regulator comprises a pressure transducer (84) and a microprocessor (88).

21. The apparatus of claim 20 wherein the exhalation valve is an electrically responsive proportional valve (82) and the flow sensor/regulator comprises the pressure transducer (84) and the microprocessor (88).

22. In an apparatus for controlling the maximum and minimum pressure at which breathable gas in inhaled and exhaled, respectively, from a high pressure source by a pilot equipped with an anti-g suit and experiencing g-force above a preselected value, the maximum and minimum pressures varying in accordance with the g-force, the combination comprising:

a face mask having a common inlet/outlet port in fluid communication with the pilot's lungs;

an inhalation valve connected between the high pressure source and the mask inlet/outlet port;

an exhalation valve connected between a low pressure region and the mask inlet/outlet port;

a pressure sensor responsive to the minimum pressure and the pressure in the mask inlet/outlet port for opening the inhalation valve and closing the exhalation valve when the pressure in the inlet/outlet port falls below the minimum pressure by a threshold of sensitivity level;

an exhalation pressure sensor responsive to the maximum pressure and the pressure in the mask inlet/outlet port for closing the inhalation valve and opening the exhalation valve when the pressure in the mask inlet/outlet port reaches the maximum value, whereby the pressure in the mask inlet/outlet port will decrease to the minimum value.

23. An improvement in the method of providing physiological protection for a pilot experiencing excessive g-force while wearing an anti-g suit, a chest bladder and a face mask with a common inlet/outlet port, the anti-g suit and chest bladder being pressurized in accordance with the g-forces, the improvement comprising:

supplying breathable air to the mask inlet/outlet port during the pilot's spontaneous inhalation phase commencing at a first pressure level and ending at a second higher pressure level; and connecting the mask inlet/outlet port to a low pressure region during the pilot's exhalation phase while allowing the pressure in the mask inlet/outlet port to fall from the second level to the first level whereby the stress resulting from the exhalation phase is minimized.

* * * * *